United States Patent [19]

Ross

[11] Patent Number: 5,718,721
[45] Date of Patent: Feb. 17, 1998

[54] METHOD OF RELIEVING MIGRAINE HEADACHE PAIN

[76] Inventor: Jesse Ross, 321 E. Shore Rd., Great Neck, N.Y. 11023

[21] Appl. No.: 773,233

[22] Filed: Dec. 23, 1996

[51] Int. Cl.⁶ ..................................................... A61N 1/00
[52] U.S. Cl. ..................................................... 607/46; 607/2
[58] Field of Search .................................. 607/2, 46, 71, 607/72

[56] References Cited

U.S. PATENT DOCUMENTS

| | | | |
|---|---|---|---|
| 3,043,310 | 7/1962 | Milinowski . | |
| 4,509,521 | 4/1985 | Barry | 607/46 |
| 4,537,195 | 8/1985 | McDonnell | 607/46 |
| 4,856,526 | 8/1989 | Liss et al. | 607/71 |

OTHER PUBLICATIONS

Biological Effects of Pulsed High Peak Power Electromagnetic Energy Using Diapulse 1990.

*Primary Examiner*—Marvin M. Lateef
*Assistant Examiner*—George R. Evanisko
*Attorney, Agent, or Firm*—Myron Amer P.C.

[57] ABSTRACT

A treatment for relieving the pain of a migraine headache, known to be due to abnormally low blood flow out of the patient's brain, which eschews the use of medication and, instead, uses an electro magnetic field to cause "linear" alignment of blood nutritive elements which correspondingly increases "linear" flow thereof and thus addresses the problem without any side effects of dilution of the blood, or increase in heartbeat or otherwise as might adversely affect the health of the patient.

2 Claims, 2 Drawing Sheets

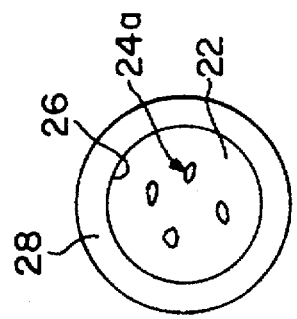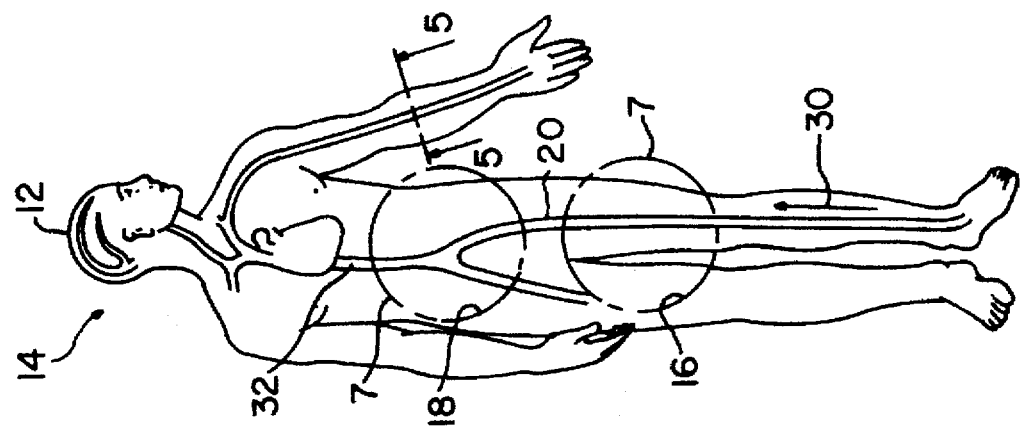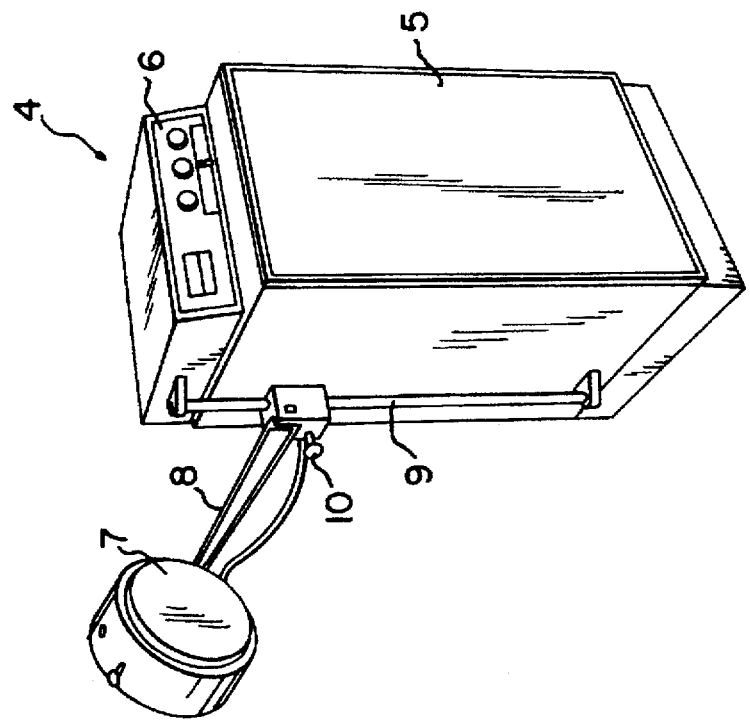

METHOD OF RELIEVING MIGRAINE HEADACHE PAIN

BACKGROUND OF THE INVENTION

The present invention relates generally to improvements in providing relief for the headache of migraine, the improvements, more particularly, eschewing the use of ingested medicines or drugs that have limitations on use and often result in adverse side effects.

The use of drugs is the treatment of choice for a migraine headache attack. Typically, the patient is given ergotamine tartrate and in most cases this will relieve the headache pain within an hour, provided the drug is administered early in the attack. This treatment, however, is recommended not be repeated more often than once weekly, and could result in a serious toxicity side effect.

Accordingly, it is recommended not to administer ergotamine to patients in septic or infectious states or who have peripheral vascular or arteriosclerotic heart disease, or to pregnant women. Despite precautions, a few patients complain of numbness and tingling of extremities and some muscle pains and tensions.

Broadly, it is an object of the present invention to overcome the foregoing and other shortcomings of the prior art.

More particularly, it is an object to avoid entirely the use of drugs in the treatment of the headache of migraine and instead to restore the blood flow which in most cases is the root cause of the medical problem.

SUMMARY OF THE INVENTION

As will be better understood as the description proceeds, underlying the present invention is the recognition that the headache of migraine is due, in many instances, to an abnormally diminished blood flow out of the patient's parietal lobe brain area and that advantageous use can be made of electromagnetic field penetration at select body locations, remote from the brain, which will increase blood flow or circulation to a pain-relieving amount to the site of the pain, thereby providing relief without any adverse side effects, such as any increase in the patient's heartbeat or any dilution of the patient's blood or having any other similar undesirable health consequence.

BRIEF DESCRIPTION OF THE DRAWINGS

The description of the invention which follows, together with the accompanying drawings should not be construed as limiting the invention to the example shown and described, because those skilled in the art to which this invention appertains will be able to devise other forms thereof within the ambit of the appended claims.

FIG. 1 is a perspective view of an apparatus for generating an electromagnetic field for practicing the within inventive method;

FIG. 4 is a graphic of blood circulation; and

FIG. 5 is a sectional view of the brachial artery as taken along line 5—5 of FIG. 4.

DESCRIPTION OF THE PREFERRED AND ILLUSTRATED EMBODIMENTS OF THE INVENTION

Figure 3:
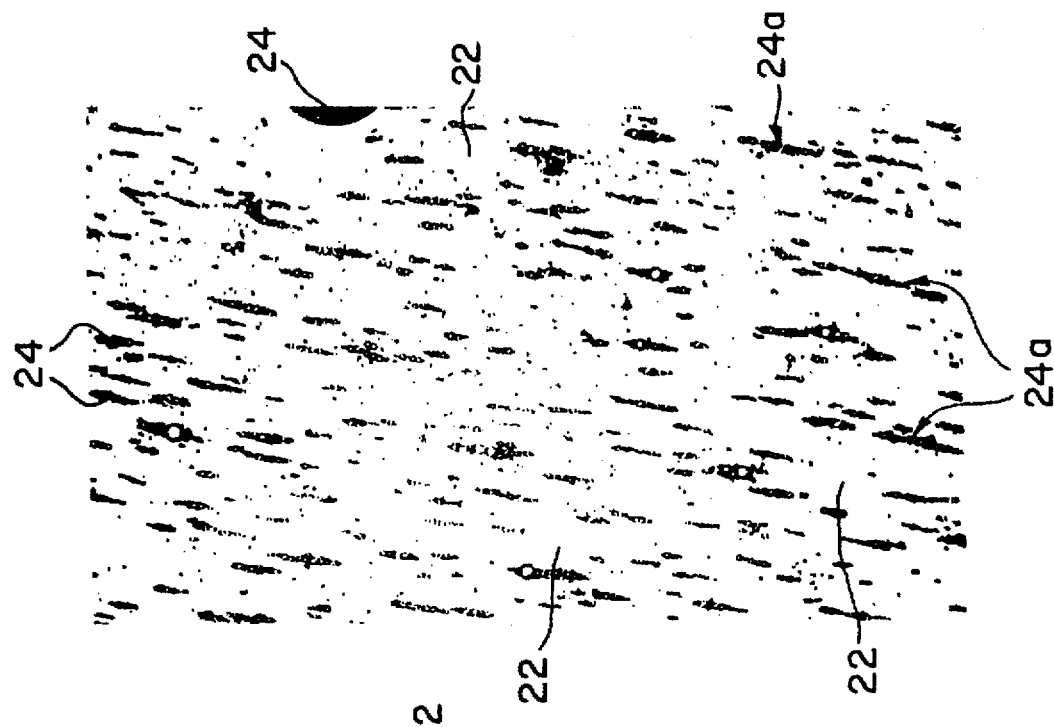
FIG. 3 is another microphotograph illustration of the blood of FIG. 2, but after subjection to the high frequency oscillation and showing a pearl chain formation of the nutritive blood elements.

Shown in FIG. 1 is an athermapeutic apparatus for the generation of pulsed high frequency oscillations to which a patient is subjected of a type which is now well known to the art wherein the pulse frequency and duration is of such nature that the total time period during which electrical energy is actually induced into the body of a patient is so short that despite the comparatively high instantaneous energy level of the pulsed power it is unaccompanied by heat generation because the time for heat dissipation is many times longer than the heat accumulation. The athermapeutic apparatus 4 as therein shown comprises a cabinet 5 provided with a control panel 6, for regulating the pulse repitition rate and pulse duration, timer setting, etc., and having a treatment head 7. Such treatment head is carried by an arm 8 to which it is pivotally connected, and with the arm in turn being reciprocally and axially movable on a tubular support 9 and secured in any desired adjusted position relative to the support 9 by a locking screw 10.

Apparatus 4 will be understood to generate an electromagnetic field having a pulse duration and frequency which is fixed at sixty five micro-seconds and for pulse frequencies of from eighty to six hundred pulses per second, so that even at its maximum setting the total peak energy of nine hundred seventy five watts maximum is of such short duration that the average power is only twenty-five to forty watts. Accordingly, at the maximum pulse rate of six hundred pulses per second the rest period between the pulses is approximately twenty-four times as great as the duration of each pulse, so that any heat that might be accumulated in the patient during the occurrence of the pulse has many times longer for its dissipation, thereby providing a treatment which is not harmful to the patient.

In the treatment use of the apparatus 4, the electromagnetic field utilized might typically have the following specific parameters:

1. A frequency of 27.12 megahertz (11 meter band);
2. A pulse repetition rate of 80 to 600 pulses per second;
3. A pulse width of 65 microseconds;
4. A power range, per pulse, of between 293 and 975 watts;
5. A duty cycle between ½ of 1% to 3.9%; and
6. A square pulse, with a rise and fall time less than 1%.

Underlying the present invention is the recognition that the generated electromagnetic field of apparatus 4 can be used to advantage to relieve migraine headache patient-experienced pain, an end use not heretofore known, without adverse side effects. More particularly, it is generally believed that the headache of migraine is due to an abnormal diminished blood flow out of the patient's brain, e.g. the parietal lobe, as noted at 12, and the advantageous use herein made of the generated electromagnetic field generated by the apparatus 4 is to increase blood flow or circulation to a pain-relieving amount to the patient's brain, without any increase in the patient's heartbeat or any dilution of the patient's blood might adversely impact on the health of the patient.

To the above end, to a patient 14 the head 7 of apparatus 4 is positioned in electromagnetic field penetrating relation to a selected body location of the patient remote from the patient's brain 12. The basis of selection of the body location is to make accessible to the generated magnetic field a main artery of the patient's circulatory system. Preferred locations that have provided good results in practice is location 16 which will be understood to be the interior portion of the thigh, i.e. femoral area, and location 18 which will be understood to be the descending colon, both locations 16 and 18 being on or adjacent to the anterior tibial 20.

Figure 2:
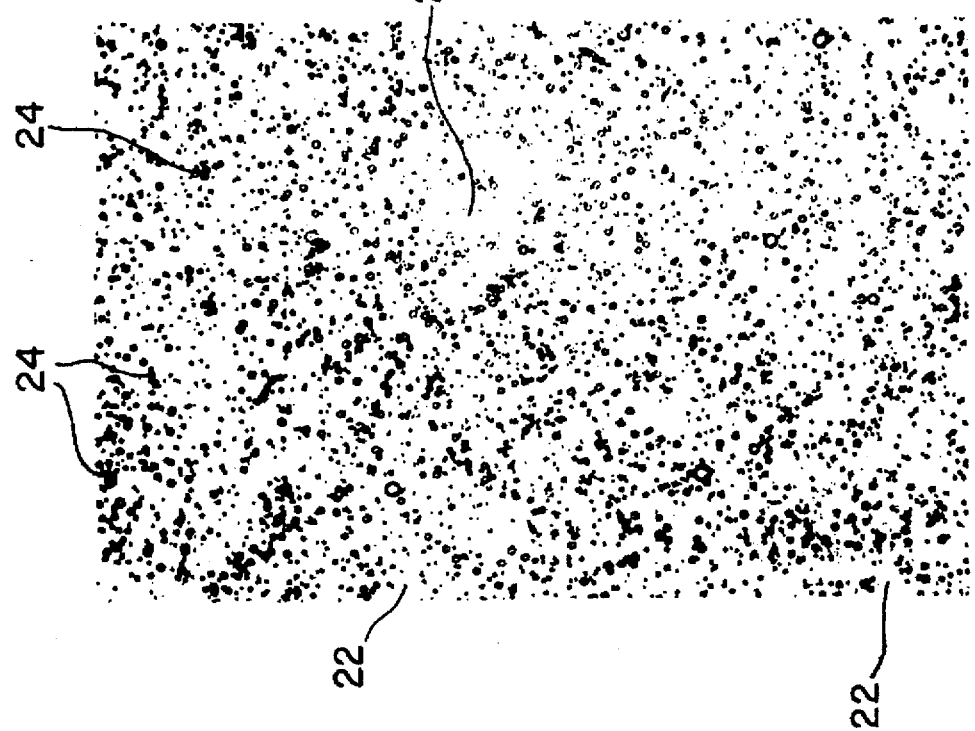
FIG. 2 is an illustration of a microphotograph of blood prior to the subjection to high frequency oscillation.

The result of the impingement of the electromagnetic field on the blood is best understood from FIGS. 2 and 3, to which reference should now be made. Blank or unoccupied areas, individually and collectively designated 22 will be understood to be the fluid content of the blood, and the occupied areas, also individually and collectively designated 24, will be understood to be the nutritive elements of which the blood is composed, such as lymph, chyle, plasma, etc.

By comparison of FIG. 2, before subjection to the electromagnetic field, to FIG. 3, after subjection, it should be readily observable that the pattern of FIG. 2 is a random dispersion of the blood fluid and nutritive elements contents 22, 24, and that in FIG. 3 the nutritive elements 24 have assumed a chain-like formation, more particularly designed 24A, which formulation is known in the parlance of the art as a "pearl chain" formulation.

A physical noteworthy attribute provided by the pearl chain formulation 24A is its longitudinal orientation which, during blood flow in the longitudinal direction of the anterior tibial 20, by way of example, is flow with minimum resistance at the interface 26 of the blood 22, 24 and the interior cell wall or cell membrane 28, which is manifested as an increase in blood flow or velocity.

More particularly, at rest the velocity, designated 30, is 5,000 ml per minute, and when in a testing run the epigastrium, or abdominal aorta 32, was exposed to a penetrating electromagnetic field, the rate of blood velocity 30 was measured to increase 1.75 times the testing pulse, which increased from the base rate of 100. It was noted that the increase occurs during treatment and is maintained 1 to 8 hours.

In practice under the circumstances described, the patient 14 felt relief from the headache of migraine without attendant abnormal increase in heartbeat or any dilution of the blood, as might adversely impact on the health of the patient.

While the apparatus for practicing the within inventive method, as well as the method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. A method of treating a patient's migraine headache pain comprising the steps of selecting as a site for treatment an interior portion of a thigh adjacent an anterior tibial of said patient having a main artery of said patient's blood circulatory system, generating an electromagnetic field into said selected site for treatment, impinging blood in said main artery in said selected site for treatment with said generated electromagnetic field, aligning by said impingement non-fluid contents of said blood in a longitudinal orientation, and flowing in a longitudinal direction through said main artery said electromagnetic field-impinged upon blood, whereby blood flow to a patient's brain is increased to a pain-relieving amount without increase in a patient's heartbeat or any dilution of said patient's blood as might adversely impact on the health of the patient.

2. A method of treating a patient's migraine headache pain comprising the steps of selecting as a site for treatment an interior portion of a descending colon adjacent the anterior fibial of said patient having a main artery of said patient's blood circulatory system, generating an electromagnetic field into said selected site for treatment, impinging blood in said main artery in said selected site for treatment with said generated electromagnetic field, aligning by said impingement non-fluid contents of said blood in a longitudinal orientation, and flowing in a longitudinal direction through said main artery said electromagnetic field-impinged upon blood, whereby blood flow to a patient's brain is increased to a pain-relieving amount without increase in a patient's heartbeat or any dilution of said patient's blood as might adversely impact on the health of the patient.

* * * * *